United States Patent [19]

Vormbrock et al.

[11] 4,400,464

[45] Aug. 23, 1983

[54] METHOD AND AGENT FOR THE STABILIZATION OF ALKALINE PHOSPHATASE

[75] Inventors: Rolf Vormbrock; Roland Helger, both of Darmstadt, Del.X

[73] Assignee: Merck Patent Gesellschaft mit beschränkter Haftung, Darmstadt, Fed. Rep. of Germany

[21] Appl. No.: 276,399

[22] Filed: Jun. 22, 1981

[30] Foreign Application Priority Data

Jun. 24, 1980 [DE] Fed. Rep. of Germany ....... 3023485

[51] Int. Cl.$^3$ ............................ C12N 9/96; C12Q 1/42
[52] U.S. Cl. ..................................... 435/21; 435/188; 435/810
[58] Field of Search ................. 435/21, 196, 188, 810

[56] References Cited

U.S. PATENT DOCUMENTS 4,132,598 1/1979 Modrovich .......................... 435/21

OTHER PUBLICATIONS

Clin. Chim. Acta 98,61 (1979), pp. 61–65.

*Primary Examiner*—Esther M. Kepplinger
*Attorney, Agent, or Firm*—Millen & White

[57] ABSTRACT

Alkaline phosphatase is stabilized in buffer solutions. This is accomplished by adding a water soluble complex of zinc ions and a chelating agent to the buffer.

9 Claims, No Drawings

METHOD AND AGENT FOR THE STABILIZATION OF ALKALINE PHOSPHATASE

BACKGROUND OF THE INVENTION

The present invention relates to a method and an agent, and also their use, for the stabilization of alkaline phosphatase in buffer solutions, e.g., as they are used in clinical chemistry for determining the enzymatic activity of alkaline phosphatase and its isoenzymes.

The determination of the enzymatic activity of alkaline phosphatase (EC 3.1.3.1) in serum or plasma plays an important part in clinical diagnosis. This determination is carried out in buffered aqueous solution and the pH of the solution should be above 8. At first, barbitone buffer (pH 8.6), and later carbonate/bicarbonate buffer (pH 9.9) or glycine/sodium hydroxide solution buffer (pH 10.5), were used. After it had been found that high concentrations of aminoalcohols, which can act as phosphoryl acceptors, increase the enzymatic activity of alkaline phosphatase, diethanolamine and 2-amino-2-methylpropan-1-ol, in particular, were employed as buffer substances in determinations of the enzymatic activity of alkaline phosphatase in clinical chemistry. However, these buffer substances are disadvantageous since they can contain impurities which inhibit or inactivate alkaline phosphatase. For diethanolamine, the impurity is ethanolamine, which can be separated off by expensive rectification. In the case of 2-amino-2-methylpropan-1-ol, a substituted ethylene derivative has been identified from a number of impurities as an inactivator of alkaline phosphatase [Clin. Chem. 24, 1,611 (1978)]. Its structure has not yet been completely elucidated.

It is known from Clin. Chim. Acta 98, 61 (1979) that the inactivation of alkaline phosphatase in 2-amino-2-methylpropan-1-ol buffer can be avoided if zinc salts are added. However, this selection is highly disadvantageous since, for concentrations of zinc ions which are greater than the optimum concentration, the alkaline phosphatase is again inhibited. Alkaline phosphatase is guaranteed to have maximum enzyme activity only if an exact dose of the zinc salts is added. This optimum concentration of added zinc ions, however, is difficult for each batch of buffer.

SUMMARY OF THE INVENTION

It is an object of this invention to provide a method and agent for stabilizing alkaline phosphatase in buffer solutions, which prevent inhibition of its enzymatic activity and which always produce optimum and reproducible results.

Upon further study of the specification and appended claims, further objects and advantages of this invention will become apparent to those skilled in the art.

These objects have been attained by this invention by providing a method for stabilizing alkaline phosphatase in buffer solutions, comprising adding a water-soluble zinc complex to the buffer solution; and preferably a method for stabilizing alkaline phosphatase in 2-amino-2-methylpropan-1-ol buffer, comprising adding a complex of zinc ions and a chelating agent to the buffer.

These objects have further been attained by this invention by providing an agent for the stabilization of alkaline phosphatase in buffer solutions, comprising a water-soluble zinc complex in addition to the buffer.

The invention further involves the use of this complex for the stabilization of alkaline phosphatase in buffer solutions.

DETAILED DISCUSSION

Surprisingly, it has been found that complexed zinc ions will stabilize the enzymatic activity of alkaline phosphatase in 2-amino-2-methylpropan-1-ol buffer just as well as zinc salts. This is so surprising primarily because it is precisely complexing agents which are otherwise responsible for the inhibition. Moreover, it is known that the inhibition of alkaline phosphatase by ethylenediaminetetraacetate can only be partially counteracted and only by adding very specific concentrations of zinc ions.

The advantages of the new stabilizers of this invention are based on the fact that, in contrast to zinc sulphate and other zinc salts, no further inhibition of the enzymatic activity of the alkaline phosphatase occurs at stabilizer concentrations of more than 0.1 mmole/liter. The optimum range of stabilizer concentration is very broad for this invention. A single stabilizer concentration can be used for various batches of buffer of different quality. The use of zinc complexes for the stabilization of alkaline phosphatase thus makes it possible to obviate the optimization of the stabilizer concentration for each particular batch of buffer.

The details of the determination of alkaline phosphatase using buffer solutions containing the new stabilizer is carried out in fully conventional manner unless indicated otherwise here. See e.g., Clin. Chem. 21, 1988 (1975) whose disclosure is incorporated by reference herein. For example, the sample to be examined is added to a thermostatted buffer solution which contains the stabilizer and magnesium ions. After a specific incubation time, the substrate is added and the change in extinction per unit time, which is proportional to the enzyme activity, is recorded using a photometer.

The pH of the buffer solutions generally is 8.5–11.

The stabilizer is a zinc chelate complex. This complex can be added as such to the buffer substance or the buffer solution; or both constituents of the complex can be added to the buffer simultaneously or successively.

Suitable zinc compounds for the preparation of complex are, in particular, any zinc salts which are soluble in water or in a solution of the complexing agent and which are compatible with, i.e., do not disturb the enzymatic determination of the alkaline phosphatase, such as zinc sulphate, zinc acetate, zinc nitrate or also zinc hydroxide and the like, and preferably zinc sulphate.

Examples of suitable chelating agents for the formation of a water-soluble zinc complex include ethylenediaminetetraacetate, trans-1,2-diamincyclohexanetetraacetate, diethylenetriaminepetaacetate or ethylene glycol bis-($\beta$-amino-ethyl ether) N,N'-tetraacetate and the like, and preferably ethylenediaminetetraacetate. The chelating agents can be employed in the form of their salts or in the acid form. Suitable zinc chelate complexes are those wherein the ligand is a compound of the formula $Ac_2N-Z-NAc_2$ wherein Z is alkylene or cycloalkylene of 2–8 C atoms and wherein any non-terminal methylene group up to 3 such methylene groups can optionally be replaced by O or N, such replacement N's optionally being substituted by acetate.

The zinc complex can be prepared by mixing the chelating agent with the zinc compound in a molar ratio of about 1:1. In this process, it is not critical whether the zinc complex is added to the buffer as the solid, for example ZnEDTA.4H$_2$O, or whether equimolar amounts of, for example, zinc sulphate and ethylenediaminetetraacetate are introduced into the buffer successively, so that the complex can be formed in the buffer solution.

The molar ratio of complex to buffer compound can be varied in the range of 1:10$^6$ to 1:10; a range of about 1:10$^4$ to 1:10$^3$ is preferred.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLES

Example 1

Examination of the influence of various stabilizer concentrations on the enzymatic activity of alkaline phosphatase.

Comparison of the stabilizing action of zinc ethylenediaminetetraacetate (ZnEDTA) with zinc sulphate.

2.8 ml of buffer solution of the following composition:

| | |
|---|---|
| 2-amino-2-methylpropan-1-ol | 0.96 mol/liter, |
| magnesium sulphate | 1.0 mmol/liter, |
| stabilizer (ZnSO$_4$ or ZnEDTA) | 10$^{-5}$ to 10$^{-2}$ mol/liter | was pipetted into a cell of 1 cm path length.

The solution was heated to a temperature of 30° C. and 0.1 ml of serum was then added. The solution was mixed and preincubated at 30° C. The preincubation time was 90 seconds for series of measurements (a) and 10 minutes for series of measurements (b). The incubation was ended by adding 0.1 ml of a solution of disodium p-nitrophenylphosphate having a concentration of 0.48 mole/liter. The solution was mixed and the activity of the alkaline phosphatase was calculated from the change in the extinction at 405 nm with time.

| Stabilizer concentration [mol/liter] | Enzyme Activity [U/liter] | | | |
|---|---|---|---|---|
| | (a) Preincubation 90 seconds | | (b) Preincubation 10 minutes | |
| | ZnSO$_4$ | ZnEDTA | ZnSO$_4$ | ZnEDTA |
| 10$^{-5}$ | 201 | 184 | 171 | 162 |
| 3.10$^{-5}$ | 209 | 191 | 186 | 184 |
| 10$^{-4}$ | 206 | 202 | 200 | 200 |
| 3.10$^{-4}$ | 201 | 205 | 205 | 202 |
| 10$^{-3}$ | 157 | 204 | 151 | 203 |
| 3.10$^{-3}$ | 11 | 200 | 18 | 199 |
| 10$^{-2}$ | 0 | 195 | 0 | 196 |

It is clearly apparent from the tables that only a narrow concentration range for optimum stabilizer action exists for the zinc salt, compared with the ZnEDTA. From a stabilizer concentration of about 10$^{-3}$ mol/liter, zinc sulphate acts as an inhibitor, and at a concentration of 10$^{-2}$ mole/liter of zinc sulphate, the enzyme activity has dropped to 0, whereas in the case of ZnEDTA, an optimum enzyme activity can still be measured.

EXAMPLE 2

Examination of the action of the stabilizers ZnSO$_4$ and ZnEDTA in buffers of different inhibitor concentrations.

From the fractional distillation of 2-amino-2-methylpropan-1-ol, fractions were obtained which inactivated alkaline phosphatase to varying extents. These fractions were used for the determination of the enzymatic activity of alkaline phosphatase in the presence of ZnSO$_4$ or ZnEDTA. The determination was carried out analogously to Example 1, with an incubation time of 90 seconds.

In the following table, the actions of the stabilizers at a concentration of 10$^{-3}$ mole/liter are compared. The enzymatic activity of the alkaline phosphatase is indicated in U/liter.

| Buffer | Enzyme activity [U/liter] | |
|---|---|---|
| | ZnSO$_4$ | ZnEDTA |
| Fraction 1 | 41 | 195 |
| Fraction 2 | 43 | 202 |
| Residue | 203 | 204 |

The table shows that the two stabilizers are equivalent at a concentration of 10$^{-3}$ mol/liter only in the distillation residue with an extremely high concentration of impurities. However, for the buffer fractions with a lower concentration of impurities, in the case of zinc sulphate, the same stabilizer concentration leads to an inhibition of the enzymatic activity of the alkaline phosphatase of about 80%, compared with ZnEDTA.

EXAMPLE 3

Examination of the suitability of various zinc complexes for the stabilization of alkaline phosphatase in 2-amino-2-methylpropan-1-ol buffer:

The determination was carried out analogously to Example 1, the stabilizer concentration being 10$^{-4}$ mole/liter in all cases; the preincubation time was 90 seconds or 10 minutes. The results are shown in the following table:

| Zinc complex ligand | Enzyme activity [U/liter] | |
|---|---|---|
| | Preincubation (a) 90 seconds | Preincubation (b) 10 minutes |
| Ethylenediaminetetraacetate | 212 | 214 |
| Trans-1,2-diaminocyclohexanetetraacetate | 213 | 206 |
| Diethylenetriaminepentaacetate | 216 | 218 |
| Ethylene glycol bis-($\beta$-amino-ethylether)-N,N'-tetraacetate | 207 | 217 |
| Without stabilizer | 180 | 82 |

It is seen that all the zinc complexes examined are suitable for the stabilization of alkaline phosphatase.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In an aminoalcohol-containing buffer solution reagent for use in the determination of the alkaline phosphatase present in a test sample brought into contact with the buffer solution, the improvement wherein the aminoalcohol-containing buffer solution further comprises the products of the addition thereto of an amount of a water-soluble zinc chelate complex effective to stabilize the alkaline phosphatase when the buffer solution is contacted with the test sample.

2. A buffer solution of claim 1 wherein the buffer solution comprises 2-amino-2-methylpropan-1-ol.

3. A buffer solution of claim 1 or 2 wherein the added zinc complex is zinc ethylenediaminetetraacetate, zinc trans-1,2-diaminocyclohexanetetraacetate, zinc diethylenetriaminepentaacetate or zinc ethylene glycol bis-($\beta$-amino-ethyl ether) N,N'-tetraacetate.

4. A buffer solution of claim 1 or 2 wherein the added zinc complex is zinc ethylenediaminetetraacetate.

5. A buffer solution of claim 1 wherein the added zinc complex is formed by adding a zinc compound and a chelating agent to the buffer solution.

6. A buffer solution of claim 1 wherein the zinc complex per se is added to the buffer solution.

7. In a method for determining the alkaline phosphatase content of a test sample by contacting the sample with an aminoalcohol-containing buffer solution, the improvement wherein the buffer solution is that of claim 1.

8. A buffer solution of claim 1 wherein the zinc complex comprises zinc chelated by a chelating agent which is a compound of the formula $Ac_2N-Z-NAc_2$ wherein Z is alkylene or cycloalkylene of 2–8 C atoms and wherein any non-terminal methylene group up to 3 such methylene groups can optionally be replaced by O or N, such replacement N's optionally being substituted by acetate.

9. A method for stabilizing the alkaline phosphatase in a buffered solution of the same containing an aminoalcohol, comprising adding to the buffered solution a stabilization effective amount of a preformed water soluble zinc chelate complex or of zinc ions and the chelating agent which make up the complex.

* * * * *